(12) United States Patent
Li et al.

(10) Patent No.: US 12,106,027 B2
(45) Date of Patent: Oct. 1, 2024

(54) METHOD AND SYSTEM OF SUDDEN WATER POLLUTANT SOURCE DETECTION BY FORWARD-INVERSE COUPLING

(71) Applicant: Dalian University of Technology, Dalian (CN)

(72) Inventors: Yu Li, Dalian (CN); Chi Zhang, Dalian (CN); Zhe Zhu, Dalian (CN)

(73) Assignee: Dalian University of Technology, Dalian (CN)

( * ) Notice: Subject to any disclaimer, the term of this patent is extended or adjusted under 35 U.S.C. 154(b) by 638 days.

(21) Appl. No.: 17/370,456

(22) Filed: Jul. 8, 2021

(65) Prior Publication Data

US 2022/0358266 A1 Nov. 10, 2022

(30) Foreign Application Priority Data

May 7, 2021 (CN) .......................... 202110495077.0

(51) Int. Cl.
*G06F 30/27* (2020.01)
*G01N 33/18* (2006.01)
(Continued)

(52) U.S. Cl.
CPC .......... *G06F 30/27* (2020.01); *G01N 33/1826* (2013.01); *G06F 18/21322* (2023.01);
(Continued)

(58) Field of Classification Search
CPC .... G06F 30/27; G06F 30/00; G06F 18/21322; G06F 18/22; G06F 18/23213;
(Continued)

(56) References Cited

U.S. PATENT DOCUMENTS 11,797,897 B2 * 10/2023 Cussonneau ......... G06Q 10/043

FOREIGN PATENT DOCUMENTS

| CN | 112149871 A | * | 12/2020 | ............. G06F 16/29 |
| CN | 112651179 A | * | 4/2021 | ............. G06F 30/27 |
| KR | 102193196 B1 | * | 12/2020 | |

OTHER PUBLICATIONS

Ghane, Alireza et al., "Location and Release Time Identification of Pollution Point Source in River Networks based on the Backward Probability Method", Jun. 1, 2016, Journal of Environmental Management 180, Elsevier Ltd. (Year: 2016).*

(Continued)

*Primary Examiner* — Cedric Johnson
(74) *Attorney, Agent, or Firm* — Gerald E. Hespos; Michael J Porco (57) ABSTRACT

The present disclosure refers to a method and a system of sudden water pollutant source detection by forward-inverse coupling, including: building an one-dimensional forward water quality simulation model of a river way according to acquired mechanical parameters and water quality parameters; according to the one-dimensional forward water quality simulation model of the river way, measuring and calculating each monitoring index by using an inverse optimization source-detection model; by constructing the one-dimensional forward water quality simulation model of the river way, using the inverse optimization source-detection model for measurement and calculation; and performing the Bayesian updating, in order to realize multi-information fusion. The present disclosure may reasonably control and use different observation information, and combine the redundancy or complementarity of multi-sourced information in space or in time to obtain consistent interpretation of the measured object, thus overcoming the uncertainty of the (Continued)

Approximate location of double-source pollutant source detection solution water environment, improving the accuracy of water pollutant source detection.

6 Claims, 9 Drawing Sheets

(51) Int. Cl.
| | | |
|---|---|---|
| G06F 18/2132 | (2023.01) | |
| G06F 18/22 | (2023.01) | |
| G06F 18/23213 | (2023.01) | |
| G06F 18/2413 | (2023.01) | |
| G06F 18/2415 | (2023.01) | |
| G06F 113/08 | (2020.01) | |
| G06Q 50/06 | (2012.01) | |

(52) U.S. Cl.
CPC ........ *G06F 18/22* (2023.01); *G06F 18/23213* (2023.01); *G06F 18/24137* (2023.01); *G06F 18/24155* (2023.01); *G06F 18/21326* (2023.01); *G06F 2113/08* (2020.01); *G06F 2219/10* (2013.01); *G06Q 50/06* (2013.01)

(58) Field of Classification Search
CPC ......... G06F 18/24137; G06F 18/24155; G06F 18/21326; G06F 2113/08; G06F 2219/10; G06F 2111/10; G06F 30/28; G01N 33/1826; G06Q 50/06; G06Q 50/26; Y02A 20/152
USPC ........................................................ 703/9, 6
See application file for complete search history.

(56) References Cited

OTHER PUBLICATIONS

Zhao, Ying et al., "A Bayesian Method for Multi-Pollution Source Water Quality Model and Seasonal Water Management in River Segments", Apr. 22, 2014, Environmental Modelling & Software 57, Elsevier, Ltd. (Year: 2014).*

* cited by examiner

| (c) | Time1/s | Location1/m | Time2/s | Location2/m |
|---|---|---|---|---|
| Ture | -200 | -15000 | -6150 | -22000 |
| decision | -202.88 | -15180.77 | -5740.00 | -23593.42 |
| Bias | -1.44% | 1.21% | 0.67% | 7.24% |

METHOD AND SYSTEM OF SUDDEN WATER POLLUTANT SOURCE DETECTION BY FORWARD-INVERSE COUPLING

TECHNICAL FIELD

The present disclosure relates to the technical field of multi-source data collection, in particular to a method and a system of sudden water pollutant source detection by forward-inverse coupling.

BACKGROUND ART

Water is the source of life and the primary foundation for maintaining the sustainable development of ecological environment. With the advancement of industrialization and new urbanization, accidental leakage and illegal discharges from industrial enterprises are threatening the water environment of small and medium-sized rivers and canals. It is of great significance to identify pollutant sources timely and accurately for dealing with sudden water pollution events.

As a typical inverse problem of environmental hydraulics, the pollutant source detection problem has been studied in many fields. Scholars at home and abroad have studied a variety of source detection algorithms for river water pollution accidents, and generally used downstream pollution monitoring information to find the most likely pollutant source in the upstream, roughly consisting of the following categories: 1) inferring a pollutant source by the tracer method or the multivariate statistical method, which is suitable for short rivers; 2) applying probability and statistics methods, such as BPM (Backward Probability Method), to identify water pollutant source terms; 3) locating pollutant sources by theoretical methods for pollutant source searches. The basic idea of these algorithms is to randomly assume source term information, then simulate the water quality concentration variation data at the monitoring station under varying source term information through a forward water quality model, and determine whether there is a real pollutant source in comparison with measured values. The efficiency of sampling methods determines the efficiency of source detection. Commonly used sampling methods include MCMC (Markov Chain Monte Carlo, Markov Monte Carlo sampling) and LHS (Latin hypercube sampling), which work well in sampling in simple rivers or canals, but are low in sampling efficiency in complex canals with the possibility of multi-sourced joint sewage discharges. Optimization algorithms, rather than random sampling, may construct rules to realize iterative calculation, and approach the optimal solution more quickly, thus improving source detection efficiency.

The problem in the prior art is that the traced pollutant sources are often not unique, the observed data attributes are different and the time-interspace is not representative enough, and the result that is relied on can only be obtained from a single data source, resulting in low accuracy of the water pollutant source detection results.

SUMMARY

The present disclosure aims at providing a method and a system for sudden water pollutant source detection by forward-inverse coupling, which is capable of reasonably controlling and using different observation information, and merging multi-sourced information, thereby improving the calculation accuracy of water pollutant source detection results.

In order to achieve the above purpose, the present disclosure provides the following scheme:

A method for sudden water pollutant source detection by forward-inverse coupling, including:

Acquiring mechanical parameters and water quality monitoring parameters of monitored waters; wherein the water quality monitoring parameters include concentration values of a plurality of monitoring indexes;

Building a one-dimensional forward water quality simulation model of a river way according to the mechanical parameters and the water quality parameters;

For any one of the monitoring indexes, using an inverse optimization source-detection model to measure and calculate the one-dimensional forward water quality simulation model of the river way, so to obtain a plurality of equivalent source detection solutions; wherein the equivalent source detection solutions include a number of pollutant sources, pollutant discharge locations, pollutant discharge intensity and pollutant discharge time;

Grouping the equivalent source detection solutions of all monitoring indexes into a first group and a second group; wherein a number of pollutant sources in the equivalent source detection solutions of the first group is 1; and a number of pollutant sources in the equivalent source detection solutions of the second group is 2;

Determining the first group as a group of equivalent source detection solutions, and clustering the pollutant discharge locations of the equivalent source detection solutions in the second group to obtain a plurality of equivalent source detection solution groups;

Updating each equivalent source detection solution group by Bayesian probability, and determining the equivalent source detection solution group with the largest posterior probability as a decision solution group.

Preferably, acquiring the mechanical parameters and the water quality monitoring parameters of the monitored waters includes:

Determining the monitored waters corresponding to the pollution monitoring station or the control section according to the natural geographical characteristics of the river basin;

Measuring the mechanical parameters and the water quality monitoring parameters of the monitored waters; wherein the mechanical parameters include: average river way width, longitudinal flow velocity and water depth of the river; and the water quality monitoring parameters also include the longitudinal diffusion coefficient and the first-order attenuation coefficient of pollutants.

Preferably, the one-dimensional forward water quality simulation model of the river way includes:

$$\frac{\partial C}{\partial t} = -U\frac{\partial C}{\partial x} - D\frac{\partial^2 C}{\partial x^2} - KC;$$

$$C(m, x, t) = \frac{m}{\sqrt{4\pi Dt}} \exp\left[-\frac{(x-Ut)^2}{4Dt} - Kt\right];$$

In the formula, U represents the longitudinal flow velocity of the river, D represents the longitudinal diffusion coefficient, K represents the first-order attenuation coefficient of pollutants, t represents the pollutant discharge time, x represents the pollutant source discharge location, c represents the pollutant source concentration at the pollutant source location x along the river way direction at the time t after a pollution event, and m represents the pollutant discharge intensity per unit area of the pollutant source.

Preferably, measuring and calculating each of the monitoring indexes respectively by using the inverse optimization source-detection model according to the one-dimensional forward water quality simulation model of the river way so to obtain a plurality of equivalent source detection solutions includes:

Determining a default pollution variable matrix of each monitoring index; wherein parameters of the default pollution variable matrix include a number of pollutant sources, pollutant discharge locations, pollutant discharge intensity and pollutant discharge time;

Respectively calculating each pollutant source by using the one-dimensional forward water quality simulation model of the river way, and superimposing calculation results to obtain a theoretical value in the case of simultaneous effects of all pollutant sources;

Calculating a residual between the theoretical value and a concentration value of the corresponding monitoring index; if the residual is less than a set threshold, taking the default pollution variable matrix as an equivalent source detection solution; if the residual is greater than or equal to the set threshold, taking the minimum residual as an optimization objective to adjust the default pollution variable matrix by a genetic algorithm to obtain an adjusted default pollution variable matrix; recalculating theoretical value according to the adjusted default pollution variable matrix and comparing the value with the residual until the calculated theoretical value is less than the set threshold.

Preferably, clustering the pollutant discharge locations of the equivalent source detection solutions in the second group to obtain a plurality of equivalent source detection solution groups includes:

Taking two pollutant discharge locations of each equivalent source detection solution in the second group as the abscissa and the ordinate, respectively, to form a plurality of equivalent source detection points, which are then depicted in a two-dimensional coordinate system;

According to the minimum euclidean distance of each equivalent source detection point, adopting a k-means clustering algorithm for grouping so as to obtain a plurality of equivalent source detection solution groups.

Preferably, updating each equivalent source detection solution group by Bayesian probability, and determining the equivalent source detection solution group with the largest posterior probability as a decision solution group includes:

Calculating a priori probability of the equivalent source detection solution for any one of the equivalent source detection solution groups; wherein the equivalent source detection group includes equivalent source detection solutions of three monitoring indexes;

According to a priori probability of one monitoring index, updating the probability by priori probabilities of the other two monitoring indexes in turn to obtain posterior probabilities of all monitoring indexes in the equivalent source detection solution group;

Comparing all the posterior probabilities in the equivalent source detection solution group, and determining the equivalent source detection solution group with the largest posterior probability as a decision solution group.

A system of sudden water pollutant source detection by forward-inverse coupling includes:

An acquisition unit, which is used for acquiring mechanical parameters and water quality monitoring parameters of monitored waters; wherein the water quality monitoring parameters include concentration values of a plurality of monitoring indexes;

A modeling unit, which is used for building a one-dimensional forward water quality simulation model of a river way according to the mechanical parameters and the water quality parameters;

A measurement and calculation unit, which is, for any one of the monitoring indexes, used for using an inverse optimization source-detection model to measure and calculate the one-dimensional forward water quality simulation model of the river way, so to obtain a plurality of equivalent source detection solutions; wherein the equivalent source detection solutions include a number of pollutant sources, pollutant discharge locations, pollutant discharge intensity and pollutant discharge time;

A grouping unit, which is used for grouping the equivalent source detection solutions of all monitoring indexes into a first group and a second group; wherein a number of pollutant sources in the equivalent source detection solutions of the first group is 1; and a number of pollutant sources in the equivalent source detection solutions of the second group is 2;

A cluster determination unit, which is used for determining the first group as a group of equivalent source detection solutions, and clustering the pollutant discharge locations of the equivalent source detection solutions in the second group to obtain a plurality of equivalent source detection solution groups;

A probability update unit, which is used for updating each equivalent source detection solution group by Bayesian probability, and determining the equivalent source detection solution group with the largest posterior probability as a decision solution group.

Preferably, the acquisition unit includes:

A waters determination subunit, which is used for determining the monitored waters corresponding to the pollution monitoring station or the control section according to the natural geographical characteristics of the river basin;

A measurement subunit, which is used for measuring the mechanical parameters and the water quality monitoring parameters of the monitored waters; wherein the mechanical parameters include: average river way width, longitudinal flow velocity and water depth of the river; and the water quality monitoring parameters also include the longitudinal diffusion coefficient and the first-order attenuation coefficient of pollutants.

Preferably, the measurement and calculation unit includes:

A matrix acquisition subunit, which is used for determining a default pollution variable matrix of each monitoring index; wherein parameters of the default pollution variable matrix include a number of pollutant sources, pollutant discharge locations, pollutant discharge intensity and pollutant discharge time;

A calculation subunit, which is used for respectively calculating each pollutant source by using the one-dimensional forward water quality simulation model of the river way, and superimposing calculation results to obtain a theoretical value in the case of simultaneous effects of all pollutant sources;

A source detection solution determination subunit, which is used for calculating a residual between the theoretical value and a concentration value of the corresponding monitoring index; if the residual is less than a set threshold, taking the default pollution variable matrix as an equivalent source detection solution; if the residual is greater than or equal to the set threshold, taking the minimum residual as an optimization objective to adjust the default pollution variable matrix by a genetic algorithm to obtain an adjusted default pollution variable matrix; recalculating theoretical value according to the adjusted default pollution variable matrix and comparing the value with the residual until the calculated theoretical value is less than the set threshold.

Preferably, the grouping unit includes:

A depicting subunit, which is used for taking two pollutant discharge locations of each equivalent source detection solution in the second group as the abscissa and the ordinate, respectively, to form a plurality of equivalent source detection points, which are then depicted in a two-dimensional coordinate system;

A grouping subunit, which is used for, according to the minimum euclidean distance of each equivalent source detection point, adopting a k-means clustering algorithm for grouping so as to obtain a plurality of equivalent source detection solution groups.

According to embodiments provided in the present disclosure, the present disclosure discloses the following technical effects:

The present disclosure provides a method and a system of sudden water pollutant source detection by forward-inverse coupling, including the following steps: building an one-dimensional forward water quality simulation model of a river way according to acquired mechanical parameters and water quality parameters; according to the one-dimensional forward water quality simulation model of the river way, measuring and calculating each monitoring index by using an inverse optimization source-detection model; by constructing the one-dimensional forward water quality simulation model of the river way, using the inverse optimization source-detection model for measurement and calculation; and performing the Bayesian updating, in order to realize multi-information fusion. The present disclosure may reasonably control and use different observation information, and combine the redundancy or complementarity of multi-sourced information in space or in time to obtain consistent interpretation of the measured object, thus overcoming the uncertainty of the water environment, improving the accuracy of water pollutant source detection, and achieving the multi-solution decision for the water pollutant source detection problem.

BRIEF DESCRIPTION OF THE DRAWINGS

In order to illustrate the embodiments of the present disclosure or technical schemes in the prior art more clearly, the accompanying drawings required in the embodiments will be briefly introduced below. Apparently, the drawings in the following description are only some embodiments of the present disclosure, and those of ordinary skills in the art may obtain other drawings according to these drawings without creative work.

FIGS. 4(a)-4(c) are schematic diagrams of grouping equivalent solutions in an embodiment provided by the present disclosure; wherein

FIGS. 5(a)-5(c) are schematic diagrams of a multi-sourced information fusion and decision process in an embodiment provided by the present disclosure; wherein

DETAILED DESCRIPTION

Technical schemes in the embodiments of the present disclosure will be described clearly and completely with reference to the accompanying drawings thereof. Apparently, the embodiments described herein are only part of, not all of, embodiments in the present disclosure. Based on the embodiments of the present disclosure, all other embodiments obtained by those of ordinary skills in the art without creative work belong to the scope claimed by the present disclosure.

The present disclosure aims at providing a method and a system for sudden water pollutant source detection by forward-inverse coupling, which is capable of reasonably controlling and using different observation information, and merging multi-sourced information, thereby improving the calculation accuracy of water pollutant source detection results.

So that the above mentioned purposes, features and advantages of the present disclosure can be more apparently understood, the present disclosure will be further described with reference to figures and embodiments below.

Figure 1:
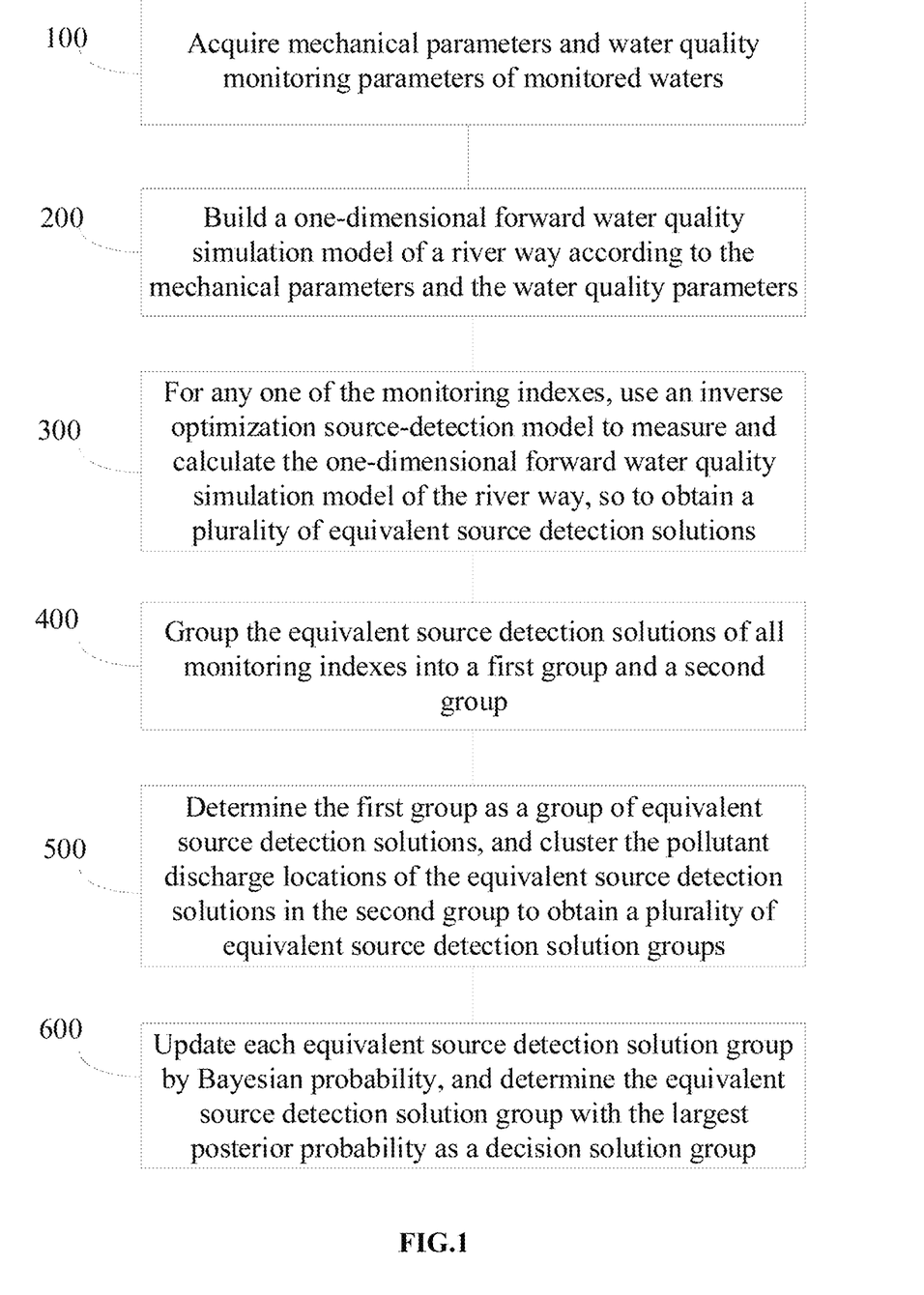
FIG. 1 is a flow chart of the method for sudden water pollutant source detection by forward-inverse coupling according to the present disclosure.

FIG. 1 is a flow chart of the method for sudden water pollutant source detection by forward-inverse coupling according to the present disclosure. As shown in FIG. 1, the method for sudden water pollutant source detection by forward-inverse coupling in the present disclosure includes:

Step 100: Acquiring mechanical parameters and water quality monitoring parameters of monitored waters; wherein the water quality monitoring parameters include concentration values of a plurality of monitoring indexes;

Step 200: Building a one-dimensional forward water quality simulation model of a river way according to the mechanical parameters and the water quality parameters;

Step 300: For any one of the monitoring indexes, using an inverse optimization source-detection model to measure and calculate the one-dimensional forward water quality simulation model of the river way, so to obtain a plurality of equivalent source detection solutions; wherein the equivalent source detection solutions include a number of pollutant sources, pollutant discharge locations, pollutant discharge intensity and pollutant discharge time;

Step 400: Grouping the equivalent source detection solutions of all monitoring indexes into a first group and a second group; wherein a number of pollutant sources in the equivalent source detection solutions of the first group is 1; and a number of pollutant sources in the equivalent source detection solutions of the second group is 2;

Step 500: Determining the first group as a group of equivalent source detection solutions, and clustering the pollutant discharge locations of the equivalent source detection solutions in the second group to obtain a plurality of equivalent source detection solution groups;

Step 600: Updating each equivalent source detection solution group by Bayesian probability, and determining the equivalent source detection solution group with the largest posterior probability as a decision solution group.

Preferably, acquiring the mechanical parameters and the water quality monitoring parameters of the monitored waters includes:

Determining the monitored waters corresponding to the pollution monitoring station or the control section according to the natural geographical characteristics of the river basin;

Measuring the mechanical parameters and the water quality monitoring parameters of the monitored waters; wherein the mechanical parameters include: average river way width, longitudinal velocity and water depth of the river; and the water quality monitoring parameters also include the longitudinal diffusion coefficient and the first-order attenuation coefficient of pollutants.

Specifically, the Step 100 includes: determining the control area corresponding to the pollution monitoring station or the control section (for example, the national control section) according to the natural geographical characteristics of the river basin, including the data of the basin stream, scope and administrative area; using ArcGIS software to obtain the basin boundary, administrative boundary and water quality section location labels of the river region; and using the Hydrology Modeling module in ArcGIS software to extract the catchment area (determine the area to be detected).

In this embodiment, the basic hydraulic parameter data in the measurement control area includes: average river way width, flow velocity, water depth, etc. Measuring parameters of basic water quality monitoring indexes include monitoring indexes and water quality parameters, wherein the monitoring indexes include concentrations of COD, ammonia nitrogen, total phosphorus, etc. Water quality parameters include the longitudinal diffusion coefficient, the first-order attenuation coefficient, and others of pollutants.

Preferably, the one-dimensional forward water quality simulation model of the river way includes:

$$\frac{\partial C}{\partial t} = -U\frac{\partial C}{\partial x} - D\frac{\partial^2 C}{\partial x^2} - KC \quad (1)$$

$$C(m, x, t) = \frac{m}{\sqrt{4\pi Dt}} \exp\left[-\frac{(x-Ut)^2}{4Dt} - Kt\right] \quad (2)$$

In the formula, U represents the longitudinal flow velocity of the river, D represents the longitudinal diffusion coefficient, K represents the first-order attenuation coefficient of pollutants, t represents the pollutant discharge time, x represents the pollutant source discharge location, c represents the pollutant source concentration at the pollutant source location x along the river way direction at the time t after a pollution event, and m represents the pollutant discharge intensity per unit area of the pollutant source.

In this embodiment, a one-dimensional forward water quality simulation model of the river way is built by using the acquired data, which is recorded as a forward procedure. For small and medium-sized rivers, the river way length is much longer than the width and depth, so the diffusion in vertical and horizontal directions can be ignored. Therefore, a one-dimensional water quality model describing the longitudinal flow can be constructed to simulate the transport procedure of pollutants along the river after an instantaneous point source pollutant discharge.

Preferably, measuring and calculating each of the monitoring indexes respectively by using the inverse optimization source-detection model according to the one-dimensional forward water quality simulation model of the river way so to obtain a plurality of equivalent source detection solutions includes:

Determining a default pollution variable matrix of each monitoring index; wherein parameters of the default pollution variable matrix include a number of pollutant sources, pollutant discharge locations, pollutant discharge intensity and pollutant discharge time;

Respectively calculating each pollutant source by using the one-dimensional forward water quality simulation model of the river way, and superimposing calculation results to obtain a theoretical value in the case of simultaneous effects of all pollutant sources;

Calculating a residual between the theoretical value and a concentration value of the corresponding monitoring index; if the residual is less than a set threshold, taking the default pollution variable matrix as an equivalent source detection solution; if the residual is greater than or equal to the set threshold, taking the minimum residual as an optimization objective to adjust the default pollution variable matrix by a genetic algorithm to obtain an adjusted default pollution variable matrix; recalculating theoretical value according to the adjusted default pollution variable matrix and comparing the value with the residual until the calculated theoretical value is less than the set threshold.

Figure 2:
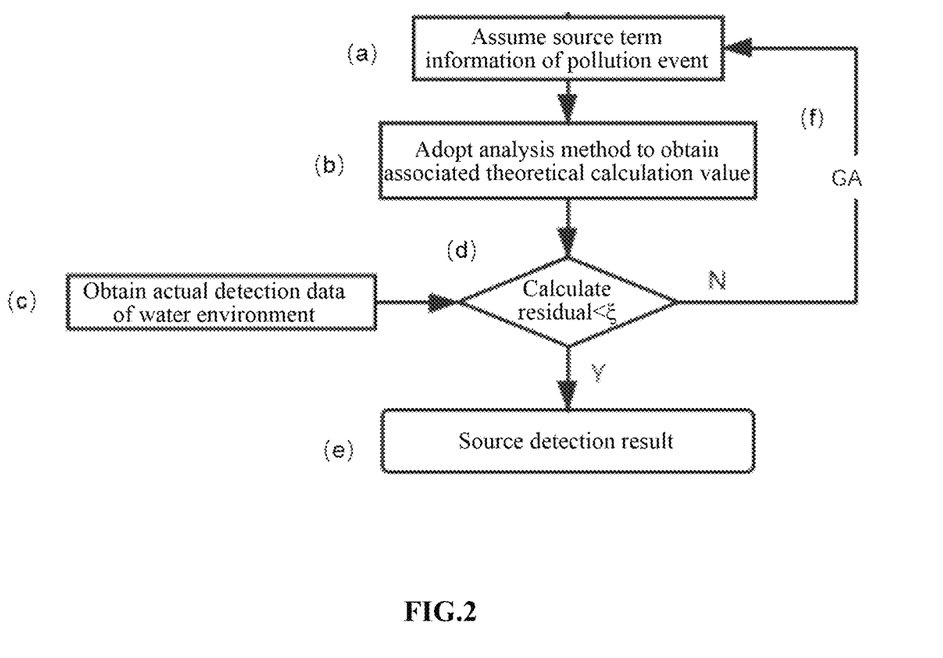
FIG. 2 is a flow chart of an inverse algorithm that couples a forward water quality model with a genetic algorithm in an embodiment provided by the present disclosure.
Figure 3:
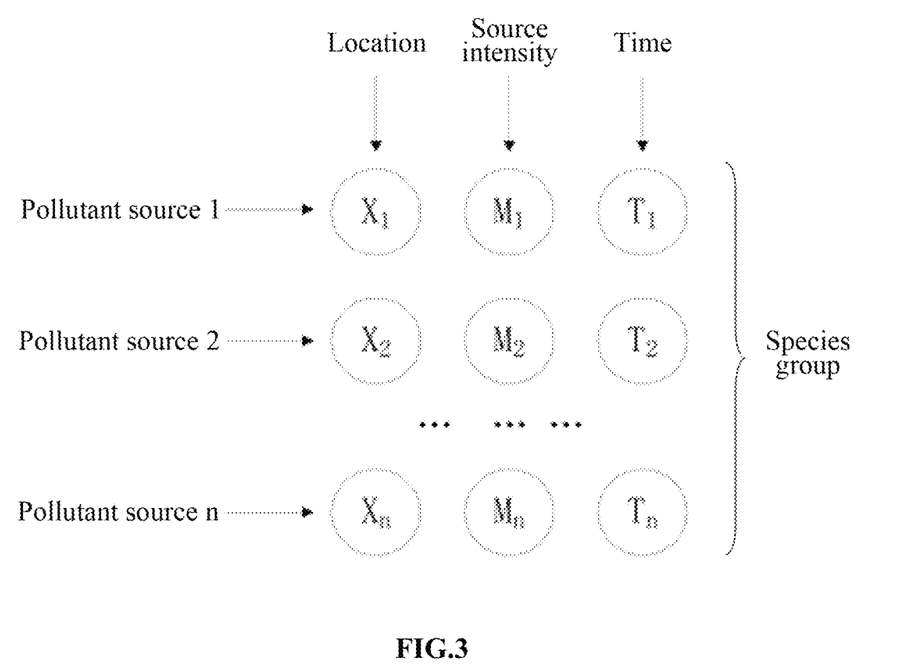
FIG. 3 is a schematic diagram of a source term information matrix about a pollution event in embodiments provided by the present disclosure.

Specifically, for a certain monitoring index, by using the forward water quality simulation model constructed in the previous step and the monitoring time series data of the pollution monitoring station within the control area (the pollutant concentration changing over time at the monitoring station), an inverse optimization source-detection model (recorded as an inverse procedure) is used to measure and calculate the pollutant source in the basin (i.e., the pollutant source position X (m), the discharge intensity M ($kg/m^2$), and the discharge time T (h)). The step proceeds as shown in FIG. 2:

(a): The source term information of a pollution event is the decision variables of the optimization algorithm, namely the pollutant discharge location X (m), the discharge intensity M ($kg/m^2$), the discharge time T (h) and the number of pollutant sources n. Herein, an n×3 matrix is randomly generated to represent the decision variables, as shown in FIG. 3. In this step, initial values of the decision variables (pollutant discharge location X (m), the discharge intensity M ($kg/m^2$), the discharge time T (h) and the number of pollutant sources n) are assumed first.

(b): An associated theoretical calculation value is obtained by the analytical method, namely the theoretical value of the simultaneous effects of n pollutant sources is obtained by calculating and superposing the assumed pollutant sources 1, 2, . . . and n by using formula (2);

(c): The actual water environment monitoring data is obtained, that is, the monitoring time series data of the pollution monitoring station in the control area described above;

(d): The residual between the measured data and the theoretical calculation value is calculated;

(e): If the residual satisfies that the error is less than the threshold, the pollutant sources assumed above are the source detection result;

(f): If the residual is greater than the threshold, the minimized residual between the forward simulated pollution process and the measured pollution process obtained according to the pollutant source term information is taken as the optimization objective by formula 3, and the genetic algorithm (GA) is used to adjust the source term information to obtain the adjusted source term information (pollutant discharge location X (m), discharge intensity M (kg/m²), discharge time T (h), and number of pollutant sources n, wherein n=1 indicates a single-source pollution, and n=2 indicates a double-source pollution):

$$\min f = \sum_{tmin}^{tmax} \left( \frac{C_t^s - C_t^o}{C_t^s + b} \right)^2 \quad (3)$$

In the formula, $C_t^o$ is the pollutant concentration monitored by the water quality monitoring station at the moment t, $C_t^s$ indicates the pollutant concentration at the water quality monitoring station at the moment t obtained through simulation by the forward water quality model (i.e., $C_s^t$ obtained by formula (2) and pollutant source information); $t_{min}$ is the initial time of a water pollution event monitored at the water quality monitoring station, and $t_{max}$ is the ending time of the water pollution event monitored at the water quality monitoring station; b is a constant set in case of the denominator 0, which is set to 1.0.

It is worth noting that due to the uncertainty of water quality model parameters, measurement uncertainty and so on, the final output "source detection result" may show multiple equivalent solutions, namely the source term information of pollutant sources is different but the objective function remains the same.

Then, the above steps are repeated to obtain all equivalent source detection solutions.

Preferably, clustering the pollutant discharge locations of the equivalent source detection solutions in the second group to obtain a plurality of equivalent source detection solution groups includes:

Taking two pollutant discharge locations of each equivalent source detection solution in the second group as the abscissa and the ordinate, respectively, to form a plurality of equivalent source detection points, which are then depicted in a two-dimensional coordinate system;

According to the minimum euclidean distance of each equivalent source detection point, adopting a k-means clustering algorithm for grouping so as to obtain a plurality of equivalent source detection solution groups.

Figure 4:
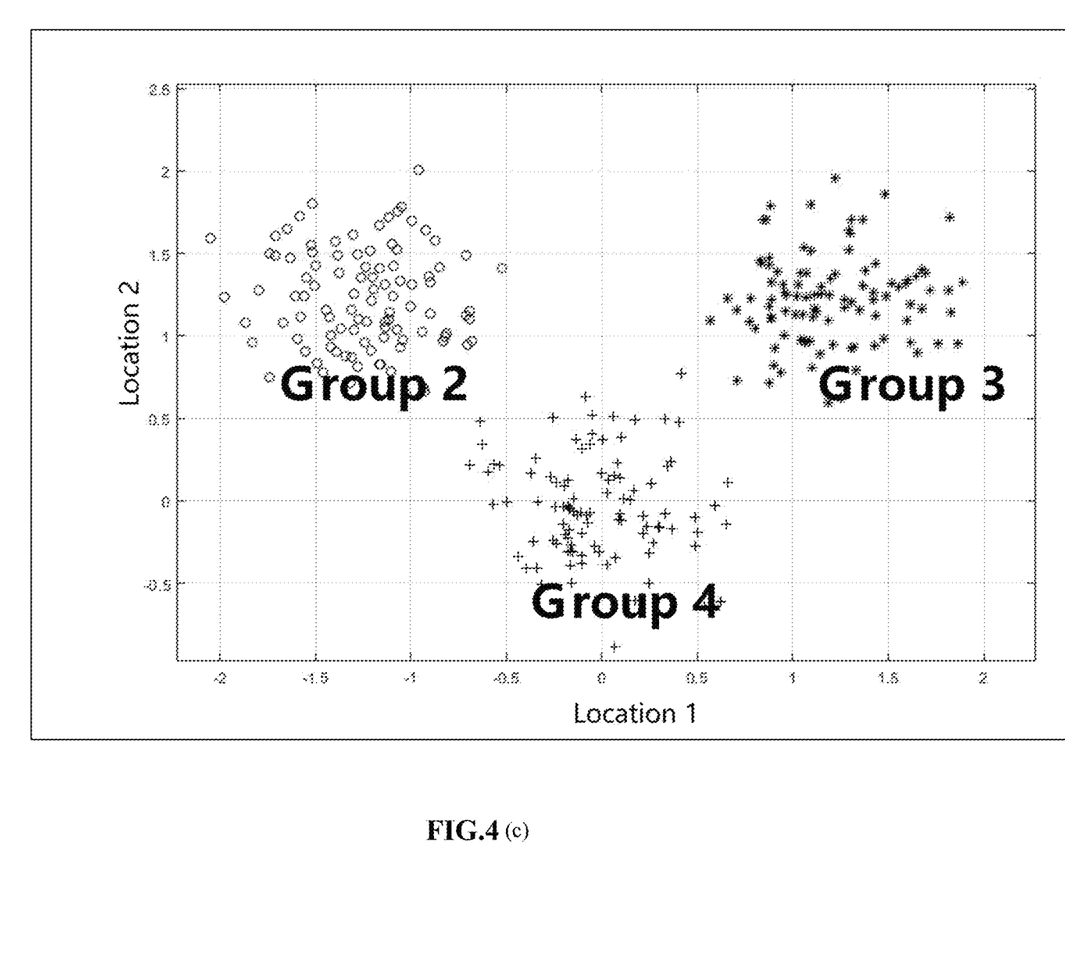
FIG. 4(a) is a schematic diagram of single-source pollution locations.
FIG. 4(b) is a schematic diagram of double-source pollution locations.
FIG. 4(c) is a schematic diagram of grouping of the double-source pollution group.
Figure 4A:
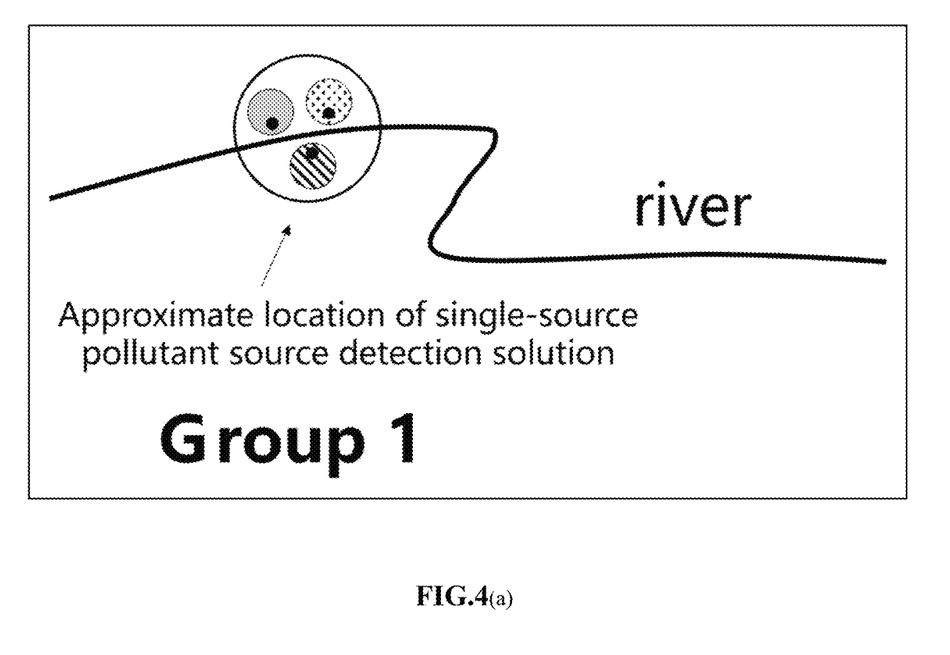
Figure 4B:
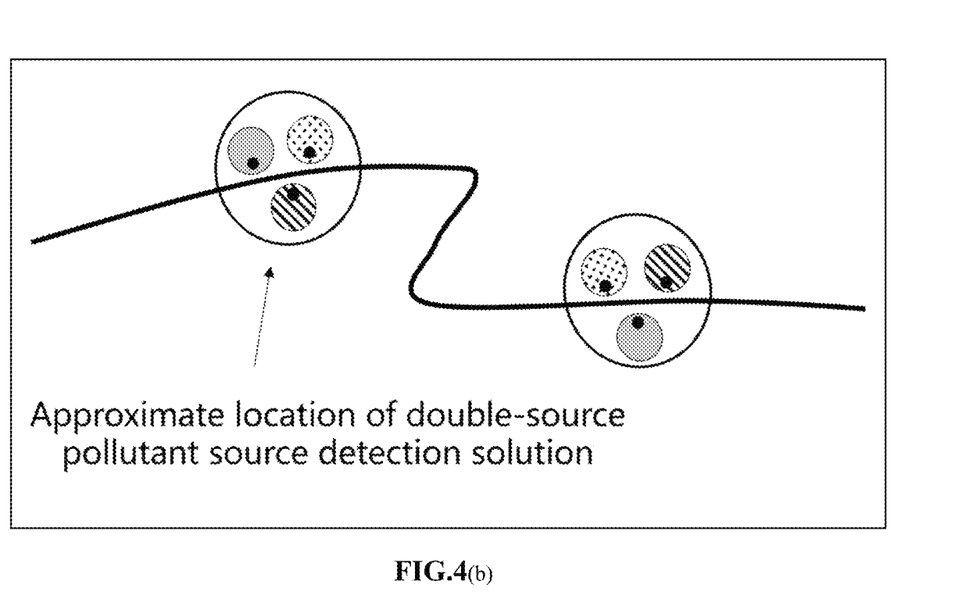

FIG. 4 is a schematic diagram of grouping equivalent solutions in an embodiment provided by the present disclosure. As shown in FIG. 4, two grouping bases are provided in this embodiment, including:

(a): Grouping basis 1, which distinguishes the solutions according to the number of pollutant sources in the solutions. The solutions with only one pollutant source detected are sorted into one group, as shown in FIG. 4(a), while the solutions with two pollutant sources detected are sorted into another group. Here are the reasons for not taking more pollutant sources into consideration. In view of the fact that the discharges from different pollutant sources are transported, merged, diffused and degraded by river ways, and are then superimposed to form the pollutant concentration data similar to the monitoring process is superimposed at the monitoring points. This process has coincidences, which also leads to the occurrence rate of double-source pollution events being much lower than that of single-source pollution events, let alone those of three-source and more-sourced pollution events. Therefore, in the practical application process, pollution events with over two sources are no longer considered.

(b): Grouping basis 2, as shown in FIG. 4(b), the double-source pollution is further grouped, wherein the locations x1 and x2 of the double-source pollution are drawn in the coordinate system as the horizontal and vertical coordinates of the coordinate system, i.e., points (x1, x2). Based on the minimum Euclidean distance between the points, the k-means clustering algorithm is used to group the points, and the group number is set to the number of source detection solutions of any pollution index, as shown by Group 2, Group 3, and Group 4 in FIG. 4(c).

Preferably, updating each equivalent source detection solution group by Bayesian probability, and determining the equivalent source detection solution group with the largest posterior probability as a decision solution group includes:

Calculating a priori probability of the equivalent source detection solution for any one of the equivalent source detection solution groups; wherein the equivalent source detection group includes equivalent source detection solutions of three monitoring indexes;

According to a priori probability of one monitoring index, updating the probability by priori probabilities of the other two monitoring indexes in turn to obtain posterior probabilities of all monitoring indexes in the equivalent source detection solution group;

Comparing all the posterior probabilities in the equivalent source detection solution group, and determining the equivalent source detection solution group with the largest posterior probability as a decision solution group.

Figure 5A:
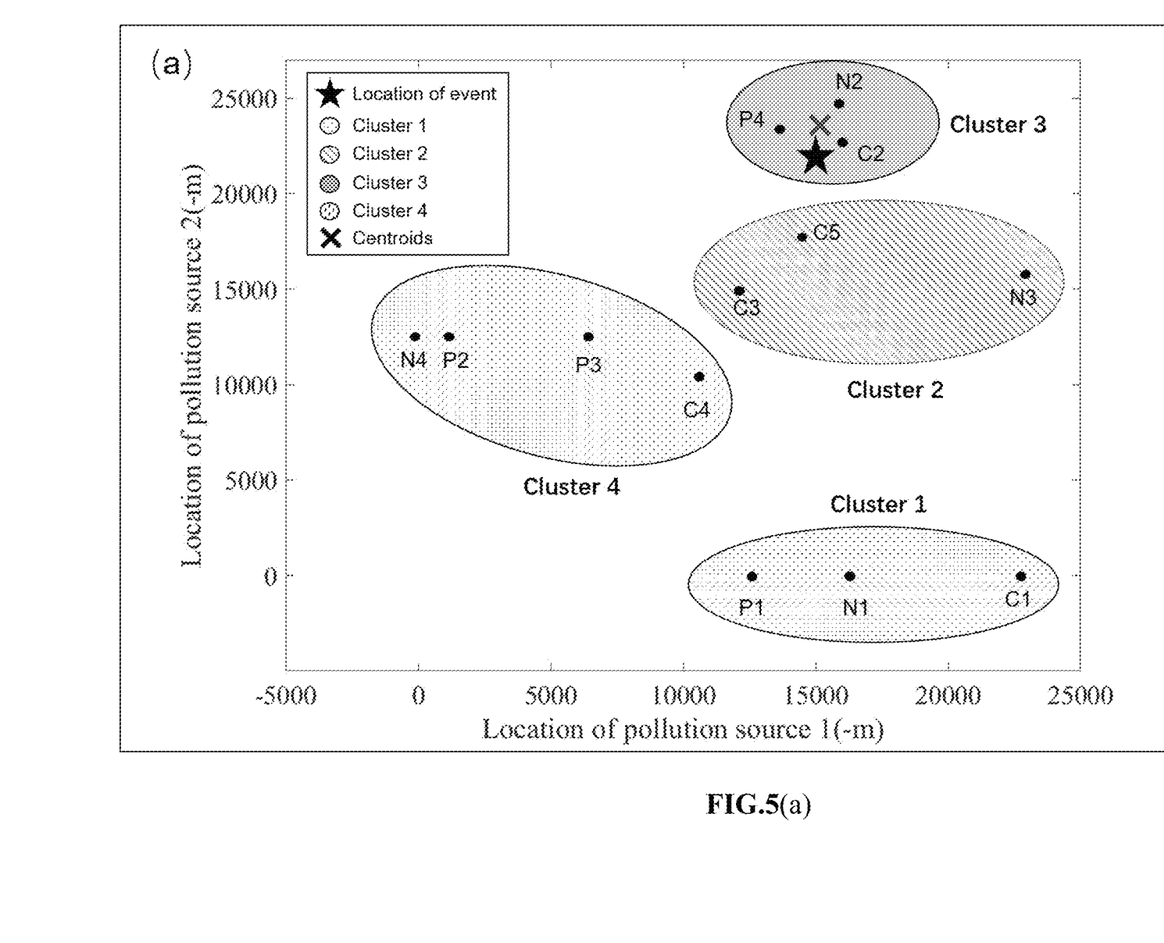
FIG. 5(a) is a schematic diagram of a multi-sourced information fusion group.
Figure 5B:
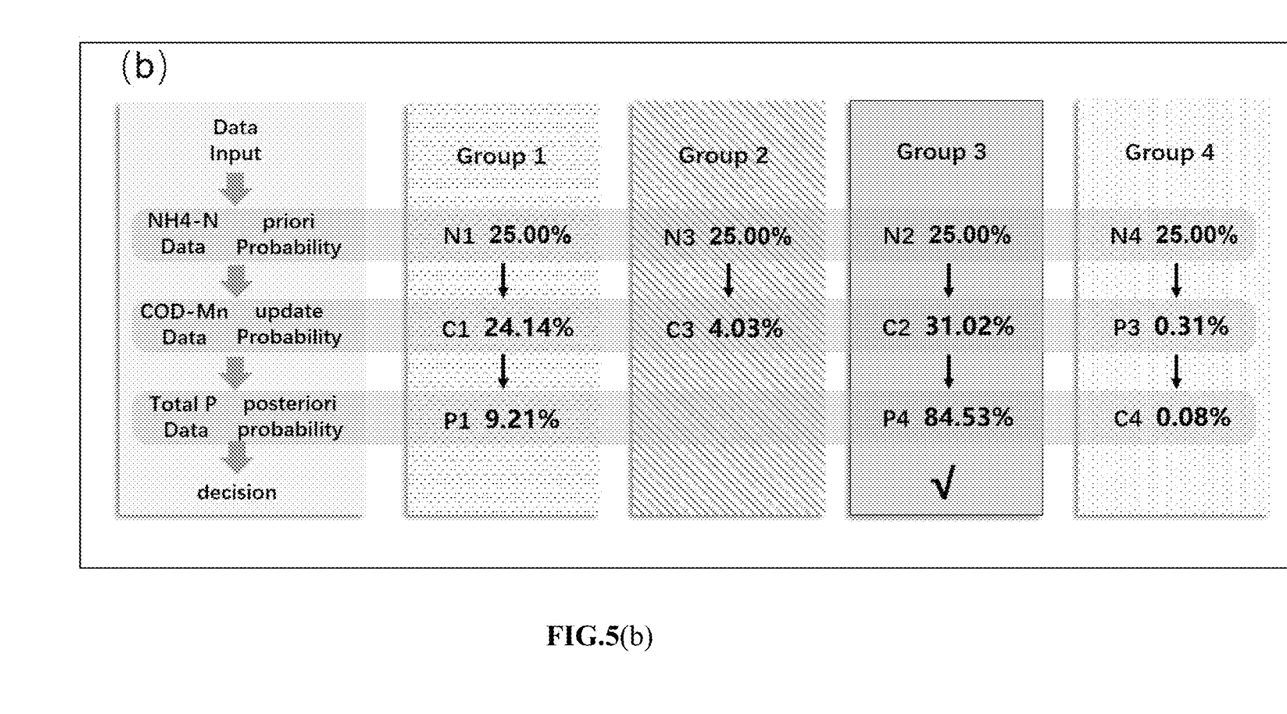
FIG. 5(b) is a schematic diagram of the probability of each group.
Figure 5C:
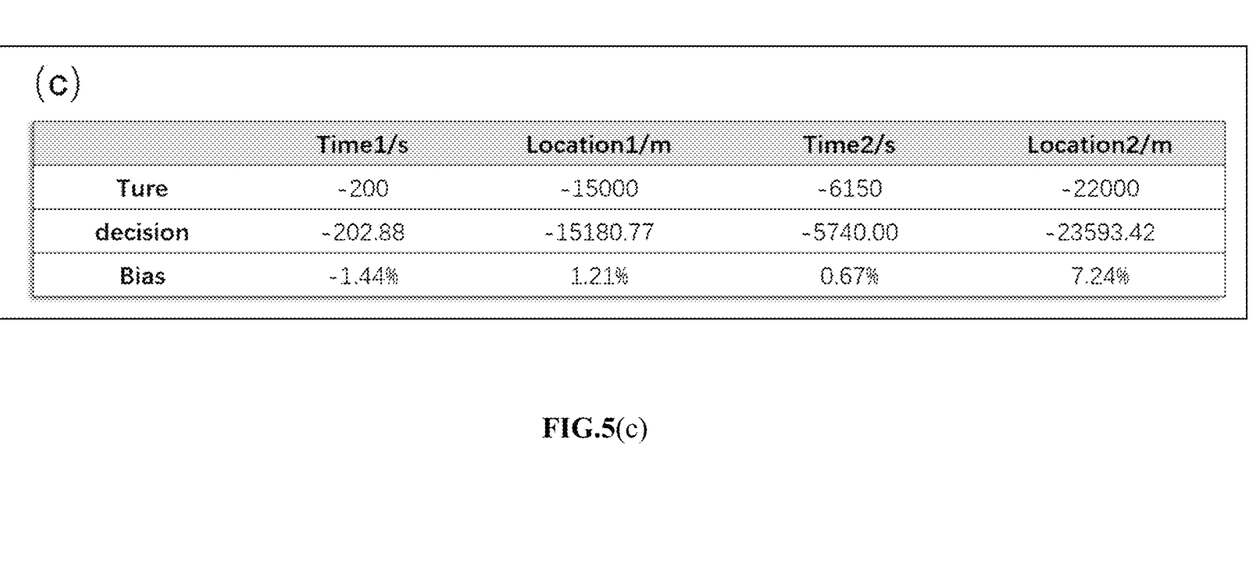
FIG. 5(c) is a schematic diagram of source term information of a pollution event.

In this embodiment, after grouping, it is assumed that each group may be a real pollutant source, so it is assumed that the initial probability of each group is equal, then the Bayesian probability updating is performed within each group, and the intra-group mean with the largest posterior probability is selected as the final decision result. The flowchart is as shown in FIG. 5:

(a): The grouping results in the previous step is summarized. In FIG. 5(a), the single-source group and double-source groups are drawn together. Cluster 1 is a single-source group, and Cluster 2, Cluster 3 and Cluster 4 are double-source groups processed by the k-means.

(b): For source detection solutions in the same group, Bayesian probability updating is carried out by using the discharge time information of pollutant sources, and the update procedure follows the example below:

Since ammonia nitrogen, total phosphorus and $COD_{Mn}$, etc. are commonly used water quality indexes for river-way water quality monitoring, ammonia nitrogen, total phosphorus and $COD_{Mn}$ are taken as examples. It is assumed that all the equivalent solutions are obtained, namely, k, m, and n equivalent solutions $(\theta_1^{NH}, \theta_2^{NH}, \ldots, \theta_k^{NH})$, $(\theta_1^{TP}, \theta_2^{TP}, \ldots, \theta_m^{TP})$, and $(\theta_1^{COD}, \theta_2^{COD}, \ldots, \theta_n^{COD})$ are obtained according to these three indexes, respectively (the right subscripts indicate the numbers of solutions, and the right superscripts indicate the pollution index categories). Here, it is believed that the equivalent solutions obtained according to the same indexes have identical initial probabilities (priori probabilities), with the priori probabilities of each solution being $P=(\theta_i^{NH})=1/k$, $P=(\theta_i^{TP})=1/m$, and $P=(\theta_i^{COD})=1/n$.

It is assumed that the discharge characteristics of pollutant sources are similar and all contain the same pollutants. There is no such case that a pollutant source discharges ammonia nitrogen only, while the other pollutant source discharges total phosphorus only. Therefore, for all the equivalent solutions mentioned above, if the discharge locations are close, they should belong to a same pollution event, and the k-means method can be used to cluster and analyze the equivalent solutions based on location information. Solutions in the same group are considered to belong to the same pollution event, so that the discharge times should be the same, namely the closer the discharge times obtained from the source detection of various pollution indexes are, the higher the probability is greater that this pollution event is true (really occurs). Based on this principle, the sequential Bayesian updating algorithm can be used to derive the posterior probability. Then, the group with the largest posterior probability is selected as the decision solution, and the mean value of the location and time information of each solution in the group is taken as the final decision.

The core of Bayesian updating is to construct a likelihood function. In order to consider the similarity of various pollution indexes in occurrence time, a likelihood function (Ortega et al., 2020) is constructed based on the Poisson distribution, which is defined as $$P = e^{-\alpha \Delta t}$$

In the formula, $\alpha$ is the defined smoothing parameter, which is set to 1.0 (Perelman et al., 2012) in this research, wherein $\Delta t$ represents the difference between the occurrence times of pollution times obtained according to two pollution indexes. When the two times are exactly the same (namely the difference is 0), and the likelihood function value is 1, it indicates that the posterior probability of this group is supported; when the larger the difference between the two times is, the smaller the likelihood function value is, and the lower the posterior probability of this group is. It is assumed that $\theta_k^{NH}$, $\theta_m^{TP}$, $\theta_n^{COD}$, and are clustered in the same group, so the posterior probability of ammonia nitrogen can be obtained by updating the ammonia nitrogen information by using the $COD_{Mn}$ information:

$$P(\theta_k^{NH} \mid \theta_m^{COD}) = \frac{P(\theta_m^{COD} \mid \theta_k^{NH}) P(\theta_k^{NH})}{P(\theta_m^{COD}) P(\theta_k^{NH}) + [1 - P(\theta_m^{COD})][1 - P(\theta_k^{NH})]}$$

In the formula, $P(\theta_k^{NH} \mid \theta_m^{COD})$ is posterior probability, $P(\theta_k^{NJ})$ is priori probability and $P(\theta_m^{COD} \mid \theta_k^{NH})$ is likelihood probability, which are calculated by the likelihood function.

When the total phosphorus information is continuously input, it is updated in the same way, and the posterior probability based on all pollution index information is finally obtained.

It can be seen from FIG. 5(b) that, for any group, ammonia nitrogen is selected as the initial index, and the initial probability of each source detection solution obtained according to ammonia nitrogen is 25%. Then update the ammonia nitrogen source detection solution by Bayesian probability using the source detection solution information obtained from the COD index in the same group. Taking Cluster 1 in gray as an example, the source detection solution of the COD index in Cluster 1 is C1. The posterior probability of N1 becomes 24.14% after calculation by the posterior probability formula. By update the ammonia nitrogen source detection solutions by Bayesian probability in the same way, the posterior probabilities of ammonia nitrogen source detection solutions in Cluster 2, Cluster 3 and Cluster 4 are 4.03%, 31.02% and 0.31%, respectively. Next, the total phosphorus index is introduced to further update the probabilities of ammonia nitrogen source detection solutions in each group. Finally, the posterior probability of N2 in Cluster 3 reaches 84.53%, which is the highest among the results of the four groups. It is believed Cluster 3 is the most possible source detection solution.

(c): The finally selected decision solution is obtained by averaging the location and time information in Cluster 3 (N2, C2, P4). Compared with the true value, it can be seen from FIG. 5(c) that the source item information of the event is as shown in the first line (True) in FIG. 5(c), and the time and location bias of the first pollutant source are −1.44% and 1.21%, respectively, while the time and location bias of the second pollutant source are 0.67% and 7.24%, respectively. As a result, it is believed that the source detection result is reasonable.

In this embodiment, all the equivalent solutions are obtained, multiple solutions are grouped, Bayesian updating process is performed in the group and a final decision is made by acquiring geographic location information, measuring parameters, building a forward procedure of water quality simulation model and optimizing inverse procedure of the source detection model, thereby embodying the multi-information fusion. The whole process can overcome the uncertainty of water environment and achieve the purpose of pollutant source detection and decision-making.

Figure 6:
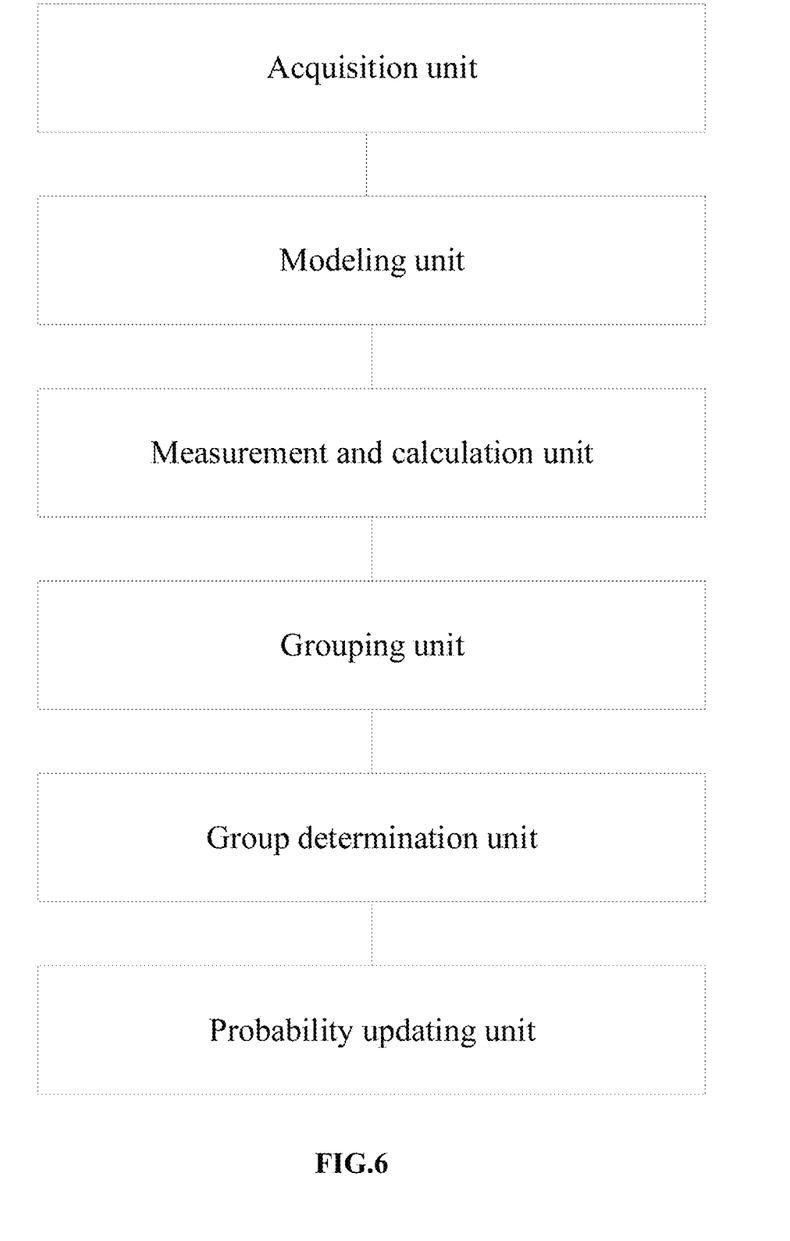
FIG. 6 is a connection schematic of the system for sudden water pollutant source detection by forward-inverse coupling according to the present disclosure.

FIG. 6 is a connection schematic of the system for sudden water pollutant source detection by forward-inverse coupling according to the present disclosure. As shown in FIG. 6, the system for sudden water pollutant source detection by forward-inverse coupling in the present disclosure includes:

An acquisition unit, which is used for acquiring mechanical parameters and water quality monitoring parameters of monitored waters; wherein the water quality monitoring parameters include concentration values of a plurality of monitoring indexes;

A modeling unit, which is used for building a one-dimensional forward water quality simulation model of a river way according to the mechanical parameters and the water quality parameters;

A measurement and calculation unit, which is, for any one of the monitoring indexes, used for using an inverse optimization source-detection model to measure and calculate the one-dimensional forward water quality simulation model of the river way, so to obtain a plurality of equivalent source detection solutions; wherein the equivalent source detection solutions include a number of pollutant sources, pollutant discharge locations, pollutant discharge intensity and pollutant discharge time;

A grouping unit, which is used for grouping the equivalent source detection solutions of all monitoring indexes into a first group and a second group; wherein a number of pollutant sources in the equivalent source detection solutions of the first group is 1; and a number of pollutant sources in the equivalent source detection solutions of the second group is 2;

A cluster determination unit, which is used for determining the first group as a group of equivalent source detection solutions, and clustering the pollutant discharge locations of the equivalent source detection solutions in the second group to obtain a plurality of equivalent source detection solution groups;

A probability update unit, which is used for updating each equivalent source detection solution group by Bayesian probability, and determining the equivalent source detection solution group with the largest posterior probability as a decision solution group.

Preferably, the acquisition unit includes:

A waters determination subunit, which is used for determining the monitored waters corresponding to the pollution monitoring station or the control section according to the natural geographical characteristics of the river basin;

A measurement subunit, which is used for measuring the mechanical parameters and the water quality monitoring parameters of the monitored waters; wherein the mechanical parameters include: average river way width, longitudinal flow velocity and water depth of the river; and the water quality monitoring parameters also include the longitudinal diffusion coefficient and the first-order attenuation coefficient of pollutants.

Preferably, the measurement and calculation unit includes:

A matrix acquisition subunit, which is used for determining a default pollution variable matrix of each monitoring index; wherein parameters of the default pollution variable matrix include a number of pollutant sources, pollutant discharge locations, pollutant discharge intensity and pollutant discharge time;

A calculation subunit, which is used for respectively calculating each pollutant source by using the one-dimensional forward water quality simulation model of the river way, and superimposing calculation results to obtain a theoretical value in the case of simultaneous effects of all pollutant sources;

A source detection solution determination subunit, which is used for calculating a residual between the theoretical value and a concentration value of the corresponding monitoring index; if the residual is less than a set threshold, taking the default pollution variable matrix as an equivalent source detection solution; if the residual is greater than or equal to the set threshold, taking the minimum residual as an optimization objective to adjust the default pollution variable matrix by a genetic algorithm to obtain an adjusted default pollution variable matrix; recalculating theoretical value according to the adjusted default pollution variable matrix and comparing the value with the residual until the calculated theoretical value is less than the set threshold.

Preferably, the grouping unit includes:

A depicting subunit, which is used for taking two pollutant discharge locations of each equivalent source detection solution in the second group as the abscissa and the ordinate, respectively, to form a plurality of equivalent source detection points, which are then depicted in a two-dimensional coordinate system;

A grouping subunit, which, according to the minimum euclidean distance of each equivalent source detection point, adopts a k-means clustering algorithm for grouping so as to obtain a plurality of equivalent source detection solution groups.

In comparison to the prior art, the present disclosure has the following beneficial effects:

(1) The present disclosure does not stop at obtaining multiple equivalent solutions, but further realizes a multi-solution decision, and reaches the accuracy requirement. According to the present disclosure, multi-information fusion is constructed, which can reasonably control and use different observation information, and follow certain rules to combine the redundancy or complementarity of multi-sourced information in space or in time to obtain consistent interpretation or description of the measured object, with the fused result usually being more reliable than that obtained by only relying on a single data source.

(2) The present disclosure improves the efficiency of the traditional source detection search algorithm, especially in the case of complex river channel environment with the possibility of multi-source joint discharges, plus the need of multiple information fusion and the calculation times which is becoming greater. According to the source detection framework based on forward and inverse coupling that is constructed by the present disclosure, the traditional random sampling is replaced by an optimization algorithm, so that the samples can approach the expected solution more quickly, and the efficiency of identification of the source term information is improved.

In this specification, various embodiments are described in a progressive manner, with each embodiment focusing on its differences from other embodiments, while cross reference would be enough for those same or similar parts between the embodiments. As the system disclosed in the embodiment corresponds to the method disclosed in the embodiment, the description is relatively simple, and the correlated parts can be found in the method description.

Principles and implementation of this present disclosure are described by specific examples, and the explanation of the above embodiments is only used to help understand the method and its core idea of the present disclosure. Also, those of ordinary skills in the art may take some modifications in the specific implementation and application scope according to the idea of the present disclosure. To sum up, the content of this specification should not be construed as limiting the present disclosure.

What is claimed is:

1. A method for sudden water pollutant source detection by forward-inverse coupling, comprising:
   acquiring mechanical parameters and water quality monitoring parameters of monitored waters, wherein the water quality monitoring parameters include concentration values of a plurality of monitoring indexes;
   building a one-dimensional forward water quality simulation model of a river way according to the mechanical parameters and the water quality parameters;
   for any one of the monitoring indexes, using an inverse optimization source-detection model to measure and calculate the one-dimensional forward water quality simulation model of the river way, so to obtain a plurality of equivalent source detection solutions, wherein the equivalent source detection solutions include a number of pollutant sources, pollutant discharge locations, pollutant discharge intensity and pollutant discharge time;
   grouping the equivalent source detection solutions of all monitoring indexes into a first group and a second group: wherein a number of pollutant sources in the equivalent source detection solutions of the first group is 1, and a number of pollutant sources in the equivalent source detection solutions of the second group is 2;
   determining the first group as a group of equivalent source detection solutions, and clustering the pollutant discharge locations of the equivalent source detection solutions in the second group to obtain a plurality of equivalent source detection solution groups;
   updating each equivalent source detection solution group by Bayesian probability, and determining the equivalent source detection solution group with a largest posterior probability as a decision solution group.

2. The method for sudden water pollutant source detection by forward-inverse coupling according to claim 1, wherein acquiring the mechanical parameters and the water quality monitoring parameters of the monitored waters comprises:

determining the monitored waters corresponding to the pollution monitoring station or the control section according to the natural geographical characteristics of the river basin;

measuring the mechanical parameters and the water quality monitoring parameters of the monitored waters; wherein the mechanical parameters include: average river way width, longitudinal velocity and water depth of the river; and the water quality monitoring parameters also include a longitudinal diffusion coefficient and a first-order attenuation coefficient of pollutants.

3. The method for sudden water pollutant source detection by forward-inverse coupling according to claim 1, wherein the one-dimensional forward water quality simulation model of the river way comprises:

$$\frac{\partial C}{\partial t} = -U\frac{\partial C}{\partial x} - D\frac{\partial^2 C}{\partial x^2} - KC;$$

$$C(m, x, t) = \frac{m}{\sqrt{4\pi Dt}}\exp\left[-\frac{(x-Ut)^2}{4Dt} - Kt\right];$$

where, U represents the longitudinal flow velocity of the river, D represents the longitudinal diffusion coefficient, K represents the first-order attenuation coefficient of pollutants, t represents the pollutant discharge time, x represents the pollutant source discharge location, c represents the pollutant source concentration at the pollutant source location x along the river way direction at the time t after a pollution event, and m represents the pollutant discharge intensity per unit area of the pollutant source.

4. The method for sudden water pollutant source detection by forward-inverse coupling according to claim 1, wherein measuring and calculating each of the monitoring indexes respectively by using the inverse optimization source-detection model according to the one-dimensional forward water quality simulation model of the river way so to obtain a plurality of equivalent source detection solutions comprises:

determining a default pollution variable matrix of each monitoring index; wherein parameters of the default pollution variable matrix include a number of pollutant sources, pollutant discharge locations, pollutant discharge intensity and pollutant discharge time;

respectively calculating each pollutant source by using the one-dimensional forward water quality simulation model of the river way, and superimposing calculation results to obtain a theoretical value in the case of simultaneous effects of all pollutant sources;

calculating a residual between the theoretical value and a concentration value of the corresponding monitoring index; if the residual is less than a set threshold, taking the default pollution variable matrix as an equivalent source detection solution; if the residual is greater than or equal to the set threshold, taking the minimum residual as an optimization objective to adjust the default pollution variable matrix by a genetic algorithm to obtain an adjusted default pollution variable matrix, recalculating theoretical value according to the adjusted default pollution variable matrix and comparing the value with the residual until the calculated theoretical value is less than the set threshold.

5. The method for sudden water pollutant source detection by forward-inverse coupling according to claim 1, wherein clustering the pollutant discharge locations of the equivalent source detection solutions in the second group to obtain a plurality of equivalent source detection solution groups comprises:

taking two pollutant discharge locations of each equivalent source detection solution in the second group as the abscissa and the ordinate, respectively, to form a plurality of equivalent source detection points, which are then depicted in a two-dimensional coordinate system;

according to the minimum Euclidean distance of each equivalent source detection point, adopting a k-means clustering algorithm for grouping so as to obtain a plurality of equivalent source detection solution groups.

6. The method for sudden water pollutant source detection by forward-inverse coupling according to claim 1, wherein updating each equivalent source detection solution group by Bayesian probability, and determining the equivalent source detection solution group with the largest posterior probability as a decision solution group comprises:

calculating a priori probability of the equivalent source detection solution for any one of the equivalent source detection solution groups; wherein the equivalent source detection group includes equivalent source detection solutions of three monitoring indexes;

according to a priori probability of one monitoring index, updating the probability by priori probabilities of the other two monitoring indexes in turn to obtain posterior probabilities of all monitoring indexes in the equivalent source detection solution group;

comparing all the posterior probabilities in the equivalent source detection solution group, and determining the equivalent source detection solution group with the largest posterior probability as a decision solution group.

* * * * *